United States Patent
Guadillière et al.

(10) Patent No.: US 6,747,035 B2
(45) Date of Patent: Jun. 8, 2004

(54) 1-ALKYL OR 1-CYCLOALKYLTRIAZOLO[4,3-A]QUINAZOLIN-5-ONES AS PHOSPHODIESTERASE INHIBITORS

(75) Inventors: Bernard Guadillière, Nanterre (FR); Remi Lavalette, Longjumeau (FR)

(73) Assignee: Warner-Lambert LLC, Morris Plains, NJ (US)

(*) Notice: Subject to any disclaimer, the term of this patent is extended or adjusted under 35 U.S.C. 154(b) by 0 days.

(21) Appl. No.: 10/211,134

(22) Filed: Aug. 2, 2002

(65) Prior Publication Data

US 2003/0069260 A1 Apr. 10, 2003

(30) Foreign Application Priority Data

Aug. 13, 2001 (EP) .............................. 01402166

(51) Int. Cl.$^7$ ..................... C07D 487/04; A61K 31/505
(52) U.S. Cl. ........................ 514/267; 544/251
(58) Field of Search ........................ 544/251; 514/267

(56) References Cited

FOREIGN PATENT DOCUMENTS

| EP | 0076199 | 4/1983 |
|---|---|---|
| EP | 1067130 | 10/2001 |
| WO | WO0066584 | 11/2000 |

OTHER PUBLICATIONS

Simone, Oncology: Introduction, Cecil Textbook of Medicine, 20th Edition, vol. 1, pp. 1004–1010, 1996.*
Heeswijk, PubMed Abstract (Ther Drug Monit 24(3):323–31), Jun. 2002.*
Suarez et al., PubMed Abstract (Medicina (B Aires) 59(4):385–92) 1999.*
Dousa, PubMed Abstract (Kidney Int 55(1):29–62) Jan. 1999.*
Spina, PubMed Abstract (Curr Opin Investig Drugs 1(2):204–13) Oct. 2000.*
Giembycz, Phosphodiesterase 4 Inhibitors and the Treatment of Asthma, Drugs, 59(2): 193–212, Feb. 2000.*
Beavo J. A. et al., Trends Pharmacol. Sci. 1990, 11, 150–155.
Beavo J. A. et al., Molecular Pharmacol., 1994, 46, 399–405.
Doherty, Current opinion in Chemical biilogy, 1999, 3:466–473.
Mohammed et al., Anti–inflammatory & Immunodilatory Investigational Drugs, 1999, 1(1): 21–28.
Schmidt et al., clinical and Experimental allergy, 29, supplement 2, 99–109.
Nieman et al., Am J. Respir Crit Care Med, 1998, 157: A413.
Underwood et al., Eur Respir J, 1998, 12:86s.
Compton et al., Am J. Respir Crit care Med, 1999, 159:A522.
Murdoch et al., Am J. Respir Crit Care Med 1998, 157: A409.
Ram et al., In J. Prakt. Chem, 1990, 332(5), 629–39.

* cited by examiner

Primary Examiner—Deepak Rao
(74) Attorney, Agent, or Firm—Peter C. Richardson; Gregg C. Benson; Robert T. Ronau

(57) ABSTRACT

The invention relates to compounds of formula (I),

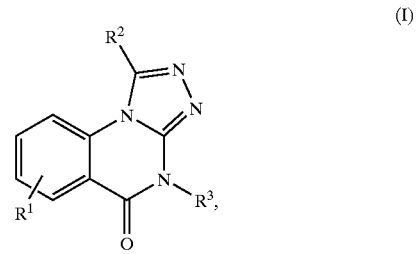

in which $R^1$, $R^2$ and $R^3$ are as defined in the description, their use as medicaments, the process for their preparation and their use for the treatment of pathologies in which therapy by a PDE4 inhibitor is relevant.

8 Claims, No Drawings

1-ALKYL OR 1-CYCLOALKYLTRIAZOLO[4, 3-A]QUINAZOLIN-5-ONES AS PHOSPHODIESTERASE INHIBITORS

This application is filed claiming priority from co-pending European Patent Application Number 01402168.1, filed Aug. 13, 2001.

FIELD OF THE INVENTION

The present invention relates to novel 1-alkyl or 1-cycloalkyltriazolo[4,3-a]quinazolin-5-ones which are useful for the preparation of medicinal products for treating complaints that fall within the domain of a treatment with a phosphodiesterase-4 (PDE4) inhibitor. These medicinal products are useful in particular as anti-inflammatory agents, antiallergic agents, bronchodilators, anti-asthmatic agents or TNFα inhibitors.

TECHNOLOGICAL BACKGROUND OF THE INVENTION

Cyclic adenosine 3', 5'-monophosphate (cAMP) is a ubiquitous intracellular second messenger, which is intermediate between a first messenger (hormone, neurotransmitter or autacoid) and the cellular functional responses: the first messenger stimulates the enzyme responsible for the synthesis of cAMP; depending on the cells concerned, the cAMP then intervenes in a great number of functions: metabolic, contractile or secretory.

The effects of cAMP end when it is degraded by cyclic nucleotide phosphodiesterases, which are intracellular enzymes that catalyze its hydrolysis into inactive adenosine 5'-monophosphate.

At least eleven major families of cyclic nucleotide phosphodiesterases (PDE) have been distinguished in mammals, numbered from 1 to 11 according to their structure, their kinetic behaviour, their substrate specificity or their sensitivity to effectors (Beavo J. A. et al. Trends Pharmacol. Sci. (1990) 11, 150–155. Beavo J. A. et al. Molecular Pharmacol. (1994) 46, 399–405). The PDE4 enzymes are specific for cAMP.

Non-specific phosphodiesterase inhibitory compounds are known, which inhibit several families of enzymes. This is the case for certain methyl xanthines such as theophylline. These compounds have a low therapeutic index, in particular on account of their action on types of PDE present in cells other than the target cells. Conversely, certain families of PDE can be selectively inhibited by various pharmacological agents: the hydrolysis of cyclic nucleotides is slowed down and their concentration thus increases in only the cells in which the type of PDE that is sensitive to the inhibitor is found.

A specific advantage is shown for the phosphodiesterases 4 (PDE4), which have been identified in many tissues including the central nervous system, the heart, vascular endothelium, vascular smooth muscle and that of the aerial pathways, myeloid lines and lymphoid lines.

An increase in cAMP in the cells involved in inflammation inhibits their activation: inhibition of the synthesis and release of mediators in mastocytes, monocytes, polymorphonuclear eosinophils and basophils, inhibition of chemotaxis and degranulation of polymorphonuclear neutrophils and eosinophils, inhibition of the proliferation and differentiation of lymphocytes.

Cytokines, in particular TNF and interleukins, produced by various types of leukocytes such as the T lymphocytes and polymorphonuclear eosinophils, play an important role in triggering inflammatory manifestations, in particular in response to stimulation by an allergen in the respiratory pathways.

Moreover, cAMP reduces the tonus of the smooth muscle fibres in the aerial pathways; PDE4 inhibitors bring about bronchorelaxation.

Chronic obstructive pulmonary disease (COPD) is a chronic pathology, of slow evolution, which is characterized by obstruction of the respiratory pathways (associated with an inflammation of the respiratory pathways and an elevated neutrophil count). The impairment in pulmonary function is for the most part irreversible (although improvements are possible by treatment with bronchodilators).

The clinical presentation of chronic obstructive pulmonary disease can vary according to the seriousness of the attack, ranging from a simple, non-incapacitating chronic bronchitis to a highly incapacitating condition of the type with chronic respiratory insufficiency. The main clinical characteristics of patients suffering from chronic obstructive pulmonary disease are chronic bronchitis and/or emphysema (associated with an inflammation of the respiratory pathways and/or an elevated neutrophil count).

In the course of recent years, selective second-generation phosphodiesterase-4 inhibitors have been proposed as agents that are potentially effective in the treatment of chronic obstructive pulmonary disease (see, inter alia, Doherty, *Current opinion in Chemical Biology* 1999, 3:466–473; Mohammed et al., *Anti-inflammatory & Immunodilatory Investigational Drugs* 1999 1(1):21–28; Schmidt et al., *Clinical and Experimental Allergy*, 29, supplement 2, 99–109).

Ariflo, a PDE4 inhibitor which is active via the oral route, has been proposed for the treatment of chronic obstructive pulmonary disease (see, inter alia: Nieman et al., Am J Respir Crit Care Med 1998, 157:A413; Underwood et al., Eur Respir J 1998, 12 :86s; Compton et al., Am J Respir Crit Care Med 1999, 159:A522. See also the oral account by Compton given at the meeting of the "European Respiratory Society" held in Madrid on Oct. 12, 1999, as well as that by Torphy and Underwood at the 4$^{th}$ world conference on inflammation, held in Paris from Jun. 27 to 30, 1999. Ariflo is currently under study, in phase III clinical trials, for the treatment of chronic obstructive pulmonary disease.

However, it should be pointed out that Ariflo has a number of drawbacks. Specifically, significant undesirable effects, such as nausea and vomiting, have been reported after administration of a dose of 20 mg as a single intake (see Murdoch et al., Am J Respir Crit Care Med 1998, 157:A409). The appearance of undesirable effects at such low doses will limit the use of Ariflo and will prevent the use of daily single-dose pharmaceutical forms, thus leading to discomfort for the patient.

Extensive research has been carried out in recent years to obtain and develop powerful PDE4 inhibitors. This turns out to be difficult due to the fact that many of the potential PDE4 inhibitors are not without activity on the phosphodiesterases of other families.

At the present time, the lack of selectivity of PDE4 inhibitors represents a major problem, given the extent of the functions regulated by cAMP. There is thus a need for powerful and selective PDE4 inhibitors, i.e. inhibitors which have no action with respect to PDEs belonging to other families.

European patent EP 0076199 describes compounds having the following general formula:

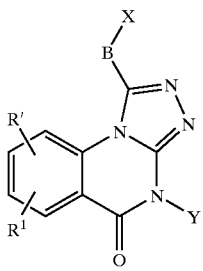

These compounds are proposed for use in the treatment of asthma, bronchitis and allergic disorders.

Patent DD 158 549 describes compounds having the following general formula:

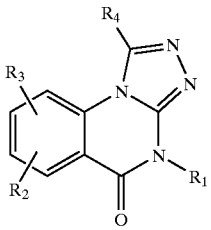

in which $R_1$ represents H, alkyl or aryl; $R_2$ and $R_3$ represent H, alkyl, halogen, OH, SH, O-alkyl or S-alkyl; $R_4$ represents H, alkyl, haloalkyl, OH, SH, O-alkyl, S-alkyl, $SO_2$-alkyl, $NH_2$, SCN, aryl or $(CH_2)_n$COOalkyl with n=0 to 2. These compounds are proposed for use as diuretics and antianaphylactic agents.

In J. Prakt. Chem, 1990, 332(5), 629–39, Ram et al. describe compounds having the following formula:

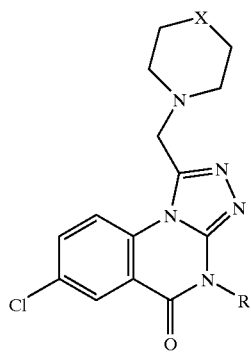

(X)

R = CH$_3$, C$_2$H$_5$
X = C, NH, N——CH$_3$, N——Ar

These compounds are proposed for use in treating hypertension.

Patent application EP 1 067 130 describes compounds having the following formula (VI)

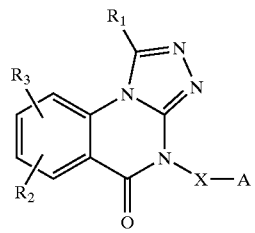

These compounds are disclosed as intermediates for synthesis.

Patent application WO 00/66584 describes compounds having the following formulas (I) and (II):

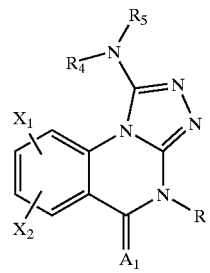

I

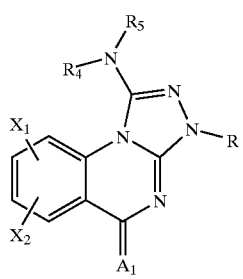

II

These compounds are proposed for use as PDE4 inhibitors.

SUMMARY OF THE INVENTION

The invention relates to a compound of formula (I),

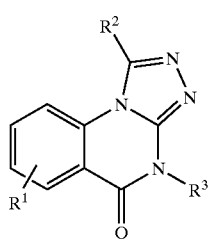

(I)

in which,
$R^1$ is selected from:
  hydroxyl, halogen, nitro, mercapto, cyano or carboxyl,
  lower alkyl or lower alkoxy, these groups being optionally substituted with 1, 2 or 3 halogen atoms, —NR$^4$R$^5$ in which R$^4$ and R$^5$ are the same or different and are selected from:
H,
lower alkyl, optionally substituted with 1, 2 or 3 groups selected from halogen, hydroxyl, cyano and lower alkoxy,
C(=O)R$^6$ in which R$^6$ is selected from:
lower alkyl optionally substituted with OR$^7$ or SR$^7$, or,
—X$_1$-cycloalkyl optionally substituted with OR$^7$, SR$^7$, NR$^7$R$^8$ or with a linear or branched C$_1$–C$_4$ alkyl,
in which R$^7$ and R$^8$ are the same or different and are selected from hydrogen or lower alkyl and X$_1$ is a single bond or a linear or branched C$_1$–C$_4$ alkylene;

R$^2$ is selected from:
lower alkyl optionally substituted with OR$^9$, SR$^9$, or,
—X$_2$-cycloalkyl optionally substituted with OR$^9$, SR$^9$, NR$^9$R$^{10}$ or with a linear or branched C$_1$–C$_4$ alkyl,
in which R$^9$ and R$^{10}$ are the same or different and are selected from hydrogen or lower alkyl and X$_2$ is a single bond or a linear or branched C$_1$–C$_4$ alkylene;

R$^3$ is selected from:

$$-(CH_2)_n-Ar\begin{matrix}Y1\\Y2\\Y3\end{matrix} \quad or \quad \diagup\hspace{-0.5em}\diagdown Ar\begin{matrix}Y1\\Y2,\\Y3\end{matrix}$$

in which:
n is an integer from 1 to 4,
Ar is an aromatic ring comprising 5 or 6 atoms including from 0 to 3 hetero atoms chosen from O, S and N,
Y1, Y2 and Y3, which may be identical or different, represent:
hydrogen, hydroxyl, mercapto, nitro, halogen, C(=O)R$^{11}$, C(=O)OR$^{11}$, C(=O)NR$^{12}$R$^{13}$, NR$^{12}$R$^{13}$ or —(CH$_2$)$_s$CN in which s is an integer from 0 to 2, R$^{11}$, R$^{12}$ and R$^{13}$ are selected from hydrogen or lower alkyl, or,
lower alkyl or lower alkoxy, each optionally substituted with 1, 2 or 3 halogen atoms, or,
—S(O)$_m$R$^{14}$ in which m is 0, 1 or 2 and R$^{14}$ is a lower alkyl;
and optionally the racemic forms and the isomeric forms thereof, as well as the pharmaceutically acceptable salts thereof, for use as a medicament.

The compounds of the present invention are useful as inhibitors, in particular as selective inhibitors, of the phosphodiesterase enzymes, and more particularly the enzyme PDE4.

The invention also relates to a process for manufacturing compounds of formula (I). The process is characterized in that it comprises:

(step 1) the reaction of a compound (1a) of general formula (1a)

in which R$^1$ is as defined above and R' represents H or lower alkyl, with a compound of general formula

R$^3$—N=C=S, in which R$^3$ is as defined above, to give a compound (1b) of general formula (1b)

in which R$^1$ and R$^3$ are as defined above, and, (step 2) the reaction of the compound (1b) obtained in step 1, with hydrazine hydrate, in an alcoholic solution, to obtain the compound (1c) of general formula, (1c)

in which R$^1$ and R$^3$ are as defined above, and, (step 3) the cyclisation of the compound (1c) obtained in step 2, by heating in the presence of a compound of formula R$^2$—C(=O)Cl, in which R$^2$ is as defined above, to obtain a compound of formula (I)

(I)

in which R$^1$, R$^2$ and R$^3$ are as defined above.

The invention also relates to a pharmaceutical composition comprising a compound of formula (I) in combination with a pharmaceutically acceptable excipient, diluent or carrier.

The invention also relates to the use of a compound of formula (I) for the preparation of a medicament for the treatment of a disease for which therapy by a PDE inhibitor, and particularly a PDE4 inhibitor, is relevant.

The invention also relates to a method for the treatment of a disease for which therapy by a PDE inhibitor, and particularly a PDE4 inhibitor, is relevant, comprising administering to a mammal, particularly a human, in need thereof, an effective amount of a compound of formula (I).

The invention also relates to new compounds of formula (I)

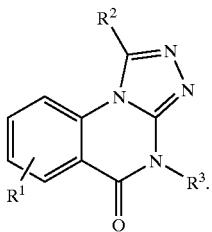

DETAILED DESCRIPTION OF THE INVENTION

The present invention thus relates to a compound of general formula (I):

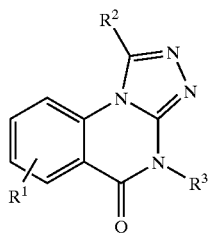

in which $R^1$, $R^2$ and $R^3$ are as defined above, for use as a medicament.

The invention also relates to new compounds of formula (I),

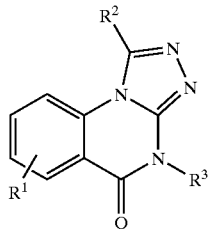

in which
$R^1$ is selected from:
  hydroxyl, halogen, nitro, mercapto, cyano or carboxyl,
  lower alkyl or lower alkoxy, these groups being optionally substituted with 1, 2 or 3 halogen atoms,
  —$NR^4R^5$ in which $R^4$ and $R^5$ are the same or different and are selected from:
    H,
    lower alkyl, optionally substituted with 1, 2 or 3 groups selected from halogen, hydroxyl, cyano and lower alkoxy,
    C(=O)$R^6$ in which $R^6$ is selected from:
      lower alkyl optionally substituted with $OR^7$ or $SR^7$ or,
      —$X_1$-cycloalkyl optionally substituted with $OR^7$, $SR^7$, $NR^7R^8$ or with a linear or branched $C_1$–$C_4$ alkyl,
        in which $R^7$ and $R^8$ are the same or different and are selected from hydrogen or lower alkyl and $X_1$ is a single bond or a linear or branched $C_1$–$C_4$ alkylene;

$R^2$ is selected from:
  lower alkyl optionally substituted with $OR^9$, $SR^9$, or,
  —$X_2$-cycloalkyl optionally substituted with $OR^9$, $SR^9$, $NR^9R^{10}$ or with a linear or branched $C_1$–$C_4$ alkyl,
    in which $R^9$ and $R^{10}$ are the same or different and are selected from hydrogen or lower alkyl and $X_2$ is a single bond or a linear or branched $C_1$–$C_4$ alkylene;

$R^3$ is selected from:

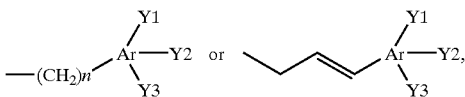

in which:
n is an integer from 1 to 4,
Ar is an aromatic ring comprising 5 or 6 atoms including from 0 to 3 hetero atoms chosen from O, S and N,
Y1, Y2 and Y3, which may be identical or different, represent:
  hydrogen, mercapto, nitro, C(=O)$R^{11}$, C(=O)O$R^{11}$, C(=O)$NR^{12}R^{13}$, $NR^{12}R^{13}$ or —$(CH_2)_s$CN in which s is an integer from 0 to 2, $R^{11}$, $R^{12}$ and $R^{13}$ are selected from hydrogen or lower alkyl, or,
  lower alkyl or lower alkoxy, each optionally substituted with 1, 2 or 3 halogen atoms, or,
  —$S(O)_mR^{14}$ in which m is 0 or 1 and $R^{14}$ is a lower alkyl, and the racemic forms and the isomeric form thereof, as well as the pharmaceutically acceptable salts thereof.

Preferably, $R^1$ is in position 7 of the quinazoline ring.
Preferably, $R^1$ is selected from
halogen or NH—$R^4$ in which $R^4$ represents:
  C(=O)$R^6$ in which $R^6$ is selected from hydrogen or lower alkyl, or,
  a lower alkyl.
Preferably, $R^1$ is selected from Br or NH—$CH_3$.
Preferably, $R^2$ is selected from:
lower alkyl optionally substituted with $OR^9$, $SR^9$, or,
  —$X_2$-cycloalkyl optionally substituted with $OR^9$, $SR^9$ or with a linear or branched $C_1$–$C_4$ alkyl,
    in which $R^9$ and $R^{10}$ are the same or different and are selected from hydrogen or lower alkyl and $X_2$ is a single bond or a linear or branched $C_1$–$C_4$ alkylene;
Preferably, $R^2$ is selected from:
lower alkyl, or,
  —$X_1$-cycloalkyl optionally substituted with a linear or branched $C_1$–$C_4$ alkyl, in which $X_1$ is a single bond or a linear or branched $C_1$–$C_4$ alkylene.
Preferably, $R^2$ is selected from methyl, cyclopentyl, cyclohexyl or cycloheptyl.
Preferably, $R^3$ is selected from benzyl or pyridine, each optionally substituted with CN.
Preferred compounds of formula (I) are those in which:
$R^1$ is selected from:
  hydroxyl, halogen, nitro, mercapto, cyano or carboxyl,
  lower alkyl or lower alkoxy, these groups being optionally substituted with 1, 2 or 3 halogen atoms,
  —$NR^4R^5$ in which $R^4$ and $R^5$ are the same or different and are selected from:
    H,
    lower alkyl, optionally substituted with 1, 2 or 3 groups chosen from halogen, hydroxyl, cyano and lower alkoxy, C(=O)R$^6$ in which R$^6$ is selected from:
  lower alkyl optionally substituted with OR$^7$ or SR$^7$ or,
  —X$_1$-cycloalkyl optionally substituted with OR$^7$, SR$^7$, NR$^7$R$^8$ or with a linear or branched C$_1$–C$_4$ alkyl,
    in which R$^7$ and R$^8$ are the same or different and are selected from hydrogen or lower alkyl and X$_1$ is a single bond or a linear or branched C$_1$–C$_4$ alkylene;

R$^2$ is selected from:
  lower alkyl, or,
  —X$_2$-cycloalkyl optionally substituted with a linear or branched C$_1$–C$_4$ alkyl,
    in which X$_2$ is a single bond or a linear or branched C$_1$–C$_4$ alkylene;

R$^3$ is selected from:

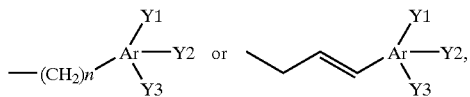

in which:
n is 1,
Ar is a phenyl or a pyridine,
Y1, Y2 and Y3, which may be identical or different, represent:
  hydrogen, methyl, methoxy, mercapto, nitro, C(=O)R$^{11}$, C(=O)OR$^{11}$, CONR$^{12}$R$^{13}$, NR$^{12}$R$^{13}$ or —(CH$_2$)$_s$CN in which s is an integer from 0 to 2 and R$^{11}$, R$^{12}$ and R$^{13}$ are selected from hydrogen or lower alkyl.

More preferred compounds of formula (I) are those in which:
R$^1$ is selected from:
  halogen or NH—R$^4$ in which R$^4$ represents:
    C(=O)R$^6$ in which R$^6$ is selected from hydrogen or lower alkyl, or,
    a lower alkyl;
R$^2$ is selected from lower alkyl or cycloalkyl;
R$^3$ represents a benzyl group optionally substituted with a group —(CH$_2$)$_s$CN in which s is an integer from 0 to 2.

Most preferred compounds of formula (I) are those in which
R$^1$ is selected from:
  halogen or NH—R$^4$ in which R$^4$ represents:
    C(=O)R$^6$ in which R$^6$ is selected from hydrogen or methyl, or,
    methyl;
R$^2$ is selected from methyl or cyclopentyl;
R$^3$ represents a benzyl group optionally substituted with CN.

In the following and in the foregoing text:
Halogen includes F, Cl, Br, I. Preferred halogen are Br and Cl.
Lower alkyl includes straight and branched carbon chains having from 1 to 6 carbon atoms. Preferred lower alkyl have from 1 to 3 carbon atoms. Examples of lower alkyl groups include methyl, ethyl, propyl, butyl, isopropyl, tert-butyl and the like.
Lower alkoxy represents a group of formula O-lower alkyl, in which said lower alkyl is as defined above. A preferred lower alkoxy is methoxy.
Cycloalkyl includes cyclic structure comprising from 3 to 7 and preferably from 5 to 7 carbon atoms. Examples of suitable cycloalkyl include cyclopropyl, cyclobutyl, cyclopentyl, cyclohexyl and cycloheptyl.
Linear or branched C$_1$–C$_4$ alkyl represents a linear or branched carbon atom chain comprising 1, 2, 3 or 4 carbon atoms.

The invention relates particularly to the following compounds:

4-benzyl-1-cyclopentyl-7-(cyclopentylformamido)-4H-[1,2,4]triazolo[4,3-a]quinazolin-5-one,
7-acetamido-4-benzyl-1-cyclopentyl-4H-[1,2,4]triazolo[4,3-a]quinazolin-5-one,
4-benzyl-7-(cyclopentylformamido)-1-methyl-4H-[1,2,4]triazolo[4,3-a]quinazolin-5-one,
7-acetamido-4-benzyl-1-methyl-4H-[1,2,4]triazolo[4,3-a]quinazolin-5-one,
4-benzyl-1-cyclopentyl-7-(N-methylacetamido)-4H-[1,2,4]triazolo[4,3-a]quinazolin-5-one,
4-benzyl-1-cyclopentyl-7-(cyclopentyl-N-methylformamido)-4H-[1,2,4]triazolo[4,3-a]quinazolin-5-one,
4-benzyl-1-cyclopentyl-7-methylamino-4H-[1,2,4]triazolo[4,3-a]quinazolin-5-one,
4-(4-cyanobenzyl)-1-cyclopentyl-7-(N-methylacetamido)-4H-[1,2,4]triazolo[4,3-a]quinazolin-5-one,
4-(4-cyanobenzyl)-1-cyclopentyl-7-(N-methylamino)-4H-[1,2,4]triazolo[4,3-a]quinazolin-5-one,
4-benzyl-7-bromo-1-cyclopentyl-4H-[1,2,4]triazolo[4,3-a]quinazolin-5-one, and,
4-benzyl-7-bromo-1-methyl-4H-[1,2,4]triazolo[4,3-a]quinazolin-5-one.

The invention also relates to the pharmaceutically acceptable salts of the compounds of formula (I). A review of the pharmaceutically acceptable salts will be found in J. Pharm. Sci., (1977), 66, 1–19. However, the expression "pharmacologically acceptable salt of a compound of formula (I) containing a basic function" means the addition salts of the compounds of formula (I) which are formed from non-toxic inorganic or organic acids such as, for example, the hydrobromic, hydrochloric, sulphuric, phosphoric, nitric, acetic, succinic, tartaric, citric, maleic, hydroxymaleic, benzoic, fumaric, toluenesulphonic and isethionic acid salts and the like. The various quaternary ammonium salts of compounds of formula (I) are also included in this category of compounds of the invention. Also, the expression "pharmacologically acceptable salt of a compound of formula (I) containing an acidic function" means the usual salts of the compounds of formula (I) which are formed from non-toxic inorganic or organic bases such as, for example, alkali metal and alkaline-earth metal (sodium, potassium, magnesium and calcium) hydroxides, amines (dibenzylethylenediamine, trimethylamine, piperidine, pyrrolidine, benzylamine and the like) or quaternary ammonium hydroxides such as tetramethylammonium hydroxide.

The PDE4 inhibitory activity of the compounds of the invention is unexpected for a skilled person. Indeed, WO 00/66584 teaches that the compound of general formula (I) have to be substituted with a group NR$_1$R$_2$ on position 1 to be active as PDE4 inhibitors. As mentioned previously, the compounds of formula (I) of the present invention are inhibitors of the enzyme phosphodiesterase and particularly of the enzyme PDE4.

In this respect, their use is recommended in the treatment of conditions or complaints which fall within the domain of a treatment by inhibition of PDE4. By way of example, the use of the compounds of the present invention may be recommended in the treatment of cancer, acquired immunodeficiency syndrome, fibrosis, excessive scarring including excessive dermal scarring such as normal or abnormal dermal scarring following wounding or surgery, osteoarthritis, osteoporosis, multiple sclerosis, anxiety, depression, atopic dermatitis, rheumatoid arthritis, septic shock, immune diseases including disseminated lupus erythematous, psoriasis, graft rejection, allergic rhinitis, diseases involving the production of TNFα, inflammatory complaints such as asthma, chronic obstructive pulmonary disease (COPD), post-ischaemic lesions, pulmonary hypertension, congestive cardiac insufficiency, acute respiratory distress syndrome, or chronic inflammatory diseases of the intestine (IBD) such as Crohn's disease and ulcerative colitis.

Pharmaceutical Formulation of the Compounds of the Invention

The compounds of the invention are administered in the form of compositions that are suitable for the nature and seriousness of the complaint to be treated. The daily dosage in man is usually between 2 mg and 1 g of product which can be absorbed in one or more intakes. The compositions are prepared by methods that are common to those skilled in the art and generally comprise 0.5% to 60% by weight of active principle (compound of formula (I)) and 40% to 99.5% by weight of pharmaceutically suitable vehicle.

The compositions of the present invention are thus prepared in forms that are compatible with the desired route of administration. For example, the following pharmaceutical forms may be envisaged, although the list given below is not limiting:

1) Forms for Oral Administration:

Drinkable solutions, suspensions, sachets of powder for drinkable solution, sachets of powder for drinkable suspension, gel capsules, gastro-resistant gel capsules, sustained-release forms, emulsions, HPMR wafer capsules or gel capsules, lyophilizates to be melted under the tongue.

2) Forms for Parenteral Administration:

Intravenous Route:

Aqueous solutions, water/co-solvent solutions, solutions using one or more solubilizing agents, colloidal suspensions, emulsions, nanoparticulate suspensions which can be used for the injection of sustained-release forms, dispersed forms and liposomes Subcutaneous/Intramuscular Route:

In addition to the forms which can be used intravenously and which can also be used for the subcutaneous and intramuscular routes, other types of form such as suspensions, dispersed forms, sustained-release gels and sustained-release implants, can also be used.

3) Forms for Topical Administration:

Among the topical forms most commonly used are creams, gels (aqueous phases gelled with polymers), patches, which are dressings to be stuck directly on the skin and which can be used to treat diseases such as dermatitis without percutaneous penetration of the active substance, sprays, emulsions and solutions.

4) Forms for Pulmonary Administration:

Included in this category are forms such as solutions for aerosols, powders for inhalers and other appropriate forms.

5) Forms for Nasal Administration:

This especially concerns solutions for nose drops.

6) Forms for Rectal Administration:

Mention will be made, inter alia, of suppositories and gels.

It may be envisaged to use forms allowing the administration of ophthalmic solutions or allowing the vaginal administration of the active principle.

Another important category of pharmaceutical form which can be used in the context of the present invention concerns forms for improving the solubility of the active principle. By way of example, it may be envisaged to use aqueous solutions of cyclodextrin, and more particularly forms comprising hydroxypropyl beta-cyclodextrin. A detailed review of this type of pharmaceutical form is presented in the article published under the reference *Journal of Pharmaceutical Sciences*, 1142–1169, 85 (11), 1996, and incorporated by way of reference in the present application.

The various pharmaceutical forms recommended above are described in detail in the book <<Pharmacie galénique [Pharmaceutical pharmacy]>> by A. LEHIR (published by Masson, 1992 ($6^{th}$ edition), which is incorporated by way of reference in the present application.

Processes for Synthesizing the Compounds of Formula (I)

The compounds according to the present invention can be obtained by carrying out several synthetic processes. Some of these synthetic processes (schemes 1–4) are described below.

The solvent, reaction time, temperature, catalyst if any, can be varied in all steps described below for all routes, as the skilled man will appreciate. Some substituents may be optionally protected in order to carry out some of the necessary steps.

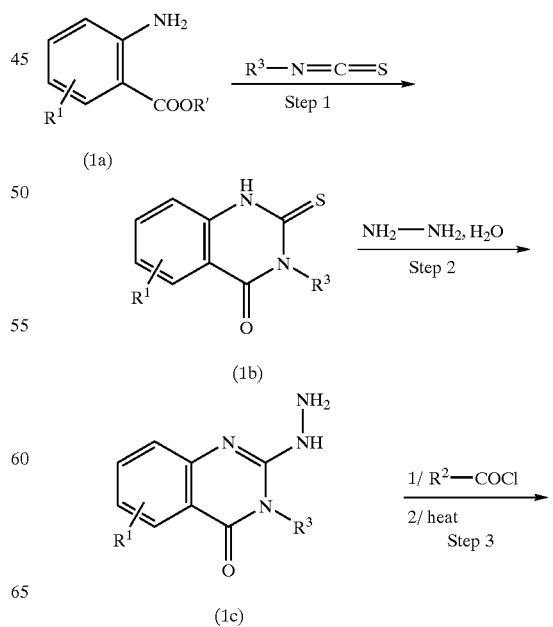

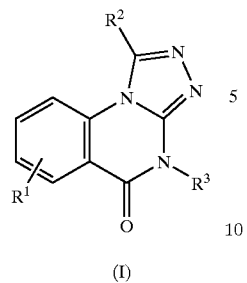

(I)

Scheme 1 describes a general process for the preparation of compounds of formula (I). In this scheme, R' is H or lower alkyl and $R^1$, $R^2$ and $R^3$ are as defined in the summary of the invention.

Compounds of formula (1a) are commercially available or may be easily synthetized by processes known from the skilled person.

In step 1, a substituted anthranilate (1a) is converted into the corresponding 1,2,3,4-tetrahydroquinazoline-2-thione-4-one (1b) by cyclisation using a suitable isothiocyanate, in a solvent such as for example pyridine or acetic acid.

In step 2, the intermediate (1b) is treated with hydrazine hydrate in an alcoholic solution, such as ethanol, to give the hydrazino derivative (1c) which, in turn, is cyclized, by heating, in the presence of an acid chloride, into a compound of formula (I) in which $R^1$, $R^2$ and $R^3$ are as defined in the summary of the invention.

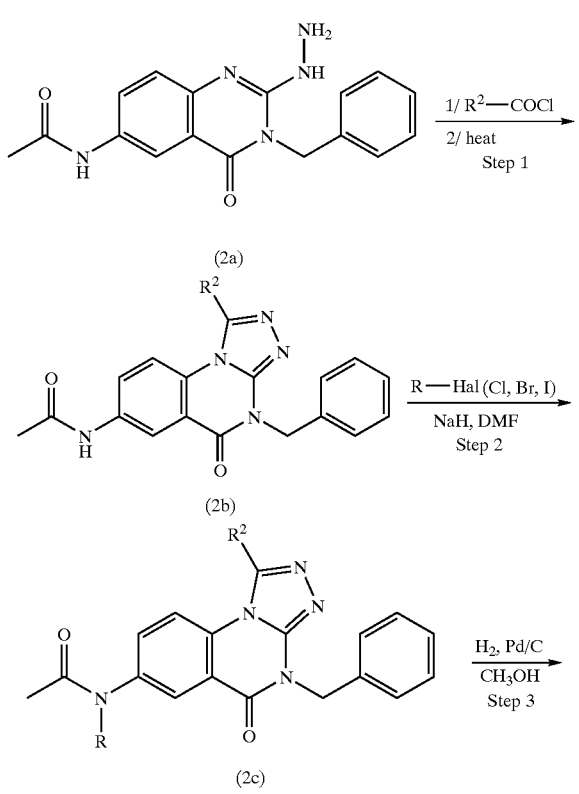

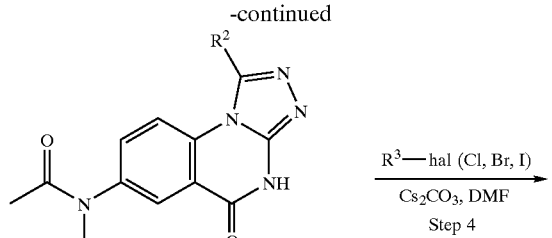

(2d)

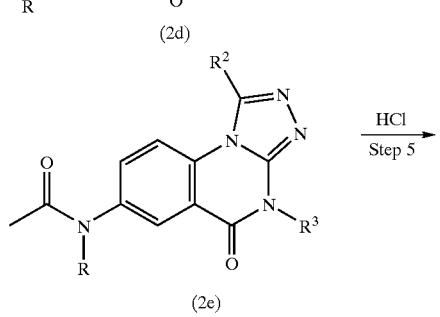

(2e)

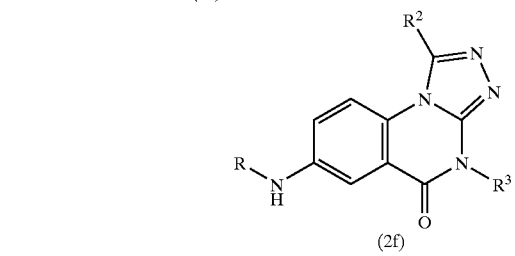

(2f)

Scheme 2 describes an alternative process for the preparation of compounds of formula (I) in which $R^1$ as N(—R)C(=O)CH$_3$ or NH—R in which R is a lower alkyl, optionally substituted. In this scheme, $R^2$ and $R^3$ are as defined in the summary of the invention.

Compound (2a) is prepared as described in step 1 and 2 of scheme 1.

In step 1, the hydrazino derivative (2a) substituted with an acetamido group in 6-position, is cyclized into the 7-acetamido-1-substituted triazolo[4,3-a]quinazoline (2b), by heating, in the presence of an acid chloride. The latter is then treated with an alkyl halide, such as alkyl iodide, in the presence of a base such as sodium hydride and in a solvent such as dimethylformamide (DMF) to give compound (2c).

In step 3, the benzyl group in 4-position of the compound (2c) is eliminated by hydrogenolysis over Pd catalyst in a solvent such as methanol, to give intermediate (2d).

In step 4, the intermediate (2d) is treated with an alkyl halide, in presence of a base, preferentially cesium carbonate, and in a solvent such as DMF, to give compound (2e) which is a compound of general formula (I) in which $R^1$ is N(—R)C(=O)CH$_3$ in which R represents a lower alkyl, optionally substituted, and $R^2$ and $R^3$ are as defined in the summary of the invention.

In step 5, the compound (2e) is treated with an acid such as diluted hydrochloric acid, to give compound (2f) which is a compound of formula (I) in which $R^1$ is NH—R in which R represents a lower alkyl, optionally substituted, and $R^2$ and $R^3$ are as defined in the summary of the invention.

Scheme 3

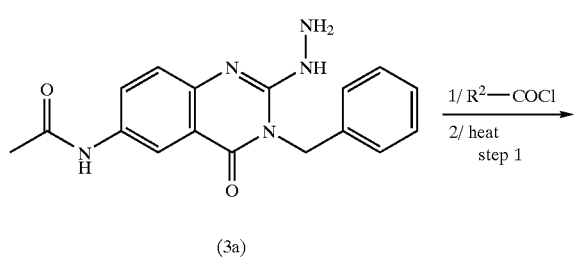

(3a)

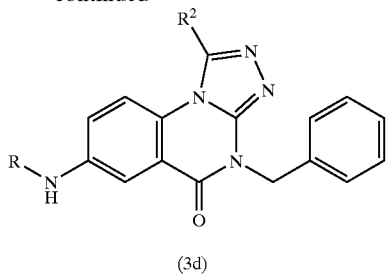

(3d)

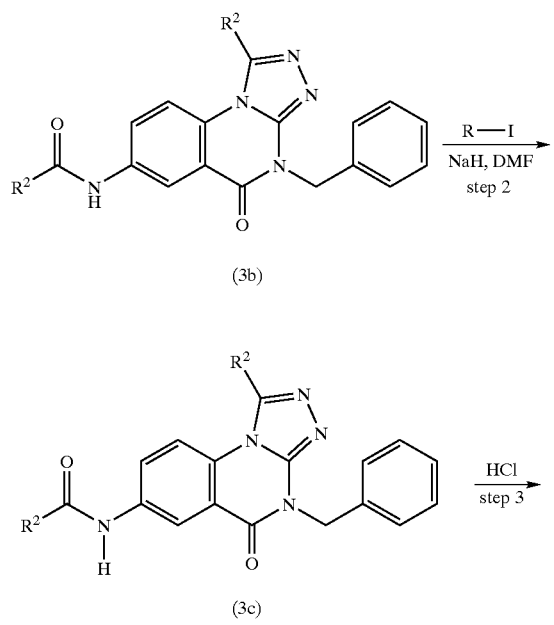

Scheme 3 describes a process for the preparation of compounds of formula (I) in which $R^3$ is benzyl and $R^1$ is NH—C(=O)—$R^2$, N(—R)—C(=O)—$R^2$ or NH—R in which R is a lower alkyl, optionally substituted and $R^2$ is as defined in the summary of the invention.

In step 1, the hydrazino derivative (3a) substituted with an acetamido group in 6-position, is treated with an excess of acid chloride to give 7-acylamino-1-substituted triazolo[4,3-a]quinazoline (3b), in which the amino function in 7-position has been transacylated. The compound (3b) is then alkylated, such as described in step 2 of scheme 2, to give compound (3c).

In step 3, compound (3c) is eventually treated with an acid such as diluted hydrochloric acid to give compound (3d) which is a compound of formula (I) in which $R^1$ is NH—R, R being a lower alkyl, optionally substituted, $R^3$ is benzyl and $R^2$ is as defined in the summary of the invention.

Scheme 4

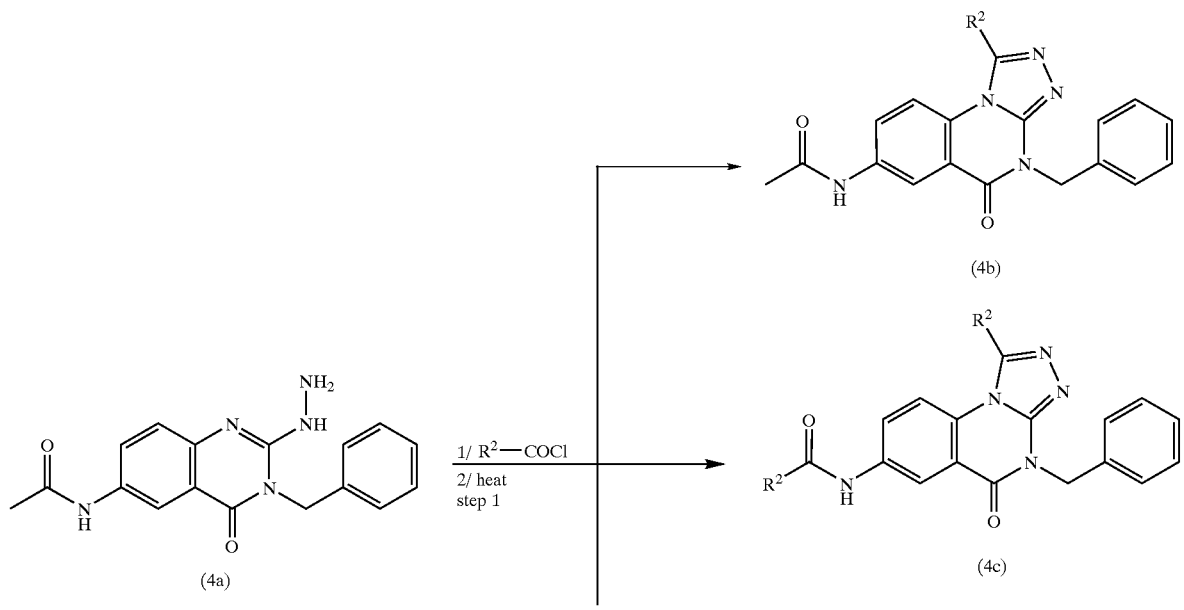

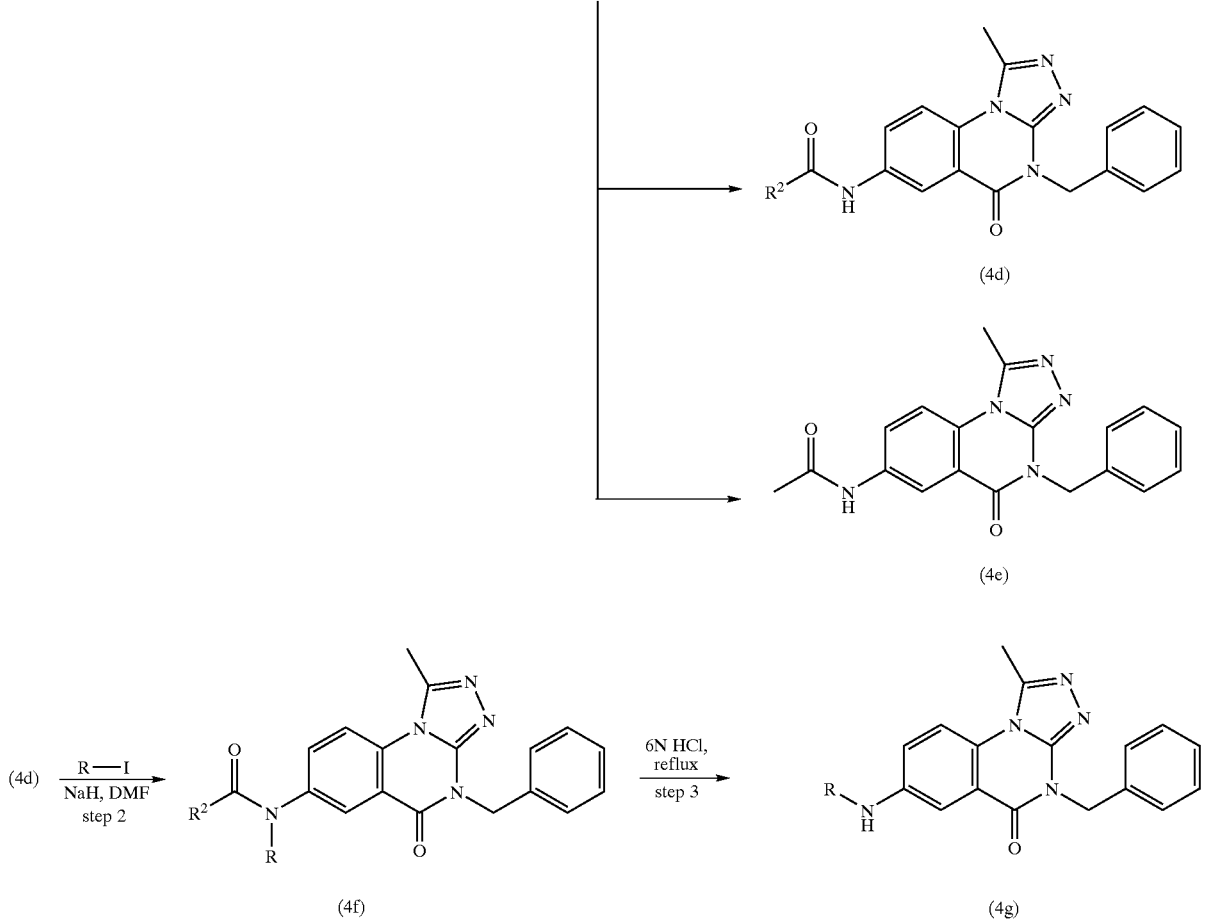

Scheme 4 describes an alternative process for the preparation of a compound of formula (I) in which $R^1$ is NHC(=O)CH$_3$, NHC(=O)R$^2$ or NH—R in which R is a lower alkyl, optionally substituted, $R^2$ is as defined in the summary of the invention and $R^3$ is benzyl.

In step 1, the hydrazino derivative (4a) substituted with an acetamido group in 6-position, is treated with an excess of acid chloride to give a mixture of compounds (4b), (4c), (4d) and (4e) which are then purified by chromatography. Each of these compounds can then be alkylated such as describes below for example (4d):

Compound (4d) is alkylated such as described in step 2 of scheme 2 to give compound (4f).

In step 3, compound (4f) is treated with an acid such as hydrochloric acid to give compound (4g) which is a compound of formula (I) in which $R^1$ is NH—R, R being a lower alkyl, optionally substituted, $R^2$ is methyl, and $R^3$ is benzyl.

EXAMPLES

Examples 1 to 11 illustrate, without limiting it, the synthesis of compounds of formula (I) according to the invention.

Example 1

4-benzyl-1-cyclopentyl-7-(cyclopentylformamido)-4H-[1,2,4]triazolo[4,3-a]quinazolin-5-one ($R^1$: 7-cyclopentylformamido, $R^2$: cyclopentyl, $R^3$: benzyl)

Example 2

7-acetamido-4-benzyl-1-cyclopentyl-4H-[1,2,4]triazolo[4,3-a]quinazolin-5-one ($R^1$: 7-acetamido, $R^2$: cyclopentyl, $R^3$: benzyl)

Example 3

4-benzyl-7-(cyclopentylformamido)-1-methyl-4H-[1,2,4]triazolo[4,3-a]quinazolin-5-one ($R^1$: 7-cyclopentylformamido, $R^2$: methyl, $R^3$: benzyl)

Example 4

7-acetamido-4-benzyl-1-methyl-4H-[1,2,4]triazolo[4,3-a]quinazolin-5-one ($R^1$: 7-acetamido, $R^2$: methyl, $R^3$: benzyl)

7.0 g (21.6 mmol) of 6-acetamido-3-benzyl-2-hydrazino-3,4-dihydro-quinazolin-4-one (synthesized according to a process described in patent application WO 00/66584) dissolved in glacial acetic acid are placed in a round-bottomed flask equipped with a stirrer and a condenser. Then, 3.15 g (23.8 mmol) of cyclopentylformyl chloride are added in a portionwise manner with stirring. The solution obtained is heated to reflux for 20 min. The solvent is evaporated off under vacuum and the residue is taken up in water.

The suspension is extracted 3 times with ethyl acetate, the combined organic phases are washed with a saturated aqueous solution of sodium chloride, dried over $Na_2SO_4$ and then concentrated under vacuum to provide a mixture of 4 compounds (distinct on Thin Layer Chromatography (TLC)).

The 4 compounds are purified by chromatography on a column of silica, eluting with a 98.5 methylene chloride/1.5 methanol mixture. The following compounds are obtained in order of elution:

1.5 g of a TLC-pure product (eluent:$CH_2Cl_2$ 94/$CH_3OH$ 6): 4-benzyl-1-cyclopentyl-7-(cyclopentylformamido)-4H-[1,2,4]triazolo[4,3-a]quinazolin-5-one (example 1):
Yield: 15.2%
TLC: Rf=0.7 ($CH_2Cl_2$ 94/$CH_3OH$ 6)
$^1H$ NMR δ(ppm): 1.55–2.0 (m, 12H); 2.05–2.25 (m, 4H); 2.7–2.8 (m, 1H); 3.55–3.65 (m, 1H); 5.5 (s, 2H); 7.2–7.3 (m, 3H); 7.65–7.7 (d, 2H); 7.75 (s, 1H); 7.8 (d. 1H); 8.1 (s, 1H); 8.5 (d, 1H).
Solvent: $CDCl_3$ 1.7 g of a TLC-pure product which is recrystallized from EtOH to give 1.45 g of 7-acetamido-4-benzyl-1-cyclopentyl-4H-[1,2,4]triazolo[4,3-a]quinazolin-5-one (example 2):
Yield: 19.6%
m.p. (Tottoli): 234° C.
TLC: $R_f$=0.45 ($CH_2Cl_2$ 94/$CH_3OH$ 6)
$^1H$ NMR δ(ppm): 1.6–1.8 (m, 4H); 2.0–2.2 (m, 4H); 2.5 (s, 3H); 3.75–3.85 (m, 1H); 5.4 (s, 2H); 7.2–7.35 (m, 3H); 7.4–7.5 (m, 2H); 8–8.15 (m, 2H); 8.55 (s, 1H); 10.35 (s, 1H).
Solvent: DMSO 0.9 g of a TLC-pure product which is recrystallized from EtOH to give 0.4 g of 4-benzyl-7-(cyclopentylformamido)-1-methyl-4H-[1,2,4]triazolo[4,3-a]quinazolin-5-one (example 3):
Yield: 10.3%
TLC: $R_f$=0.4 ($CH_2Cl_2$ 94/$CH_3OH$ 6)
$^1H$ NMR δ(ppm): 1.55–1.7 (m, 2H); 1.7–1.85 (m, 2H); 1.85–2.0 (m, 4H); 2.7–2.85 (m, 1H); 2.9 (s, 3H); 5.5 (s, 2H); 7.2–7.3 (m, 3H); 7.6 (d, 2H); 7.7 (d, 2H); 8.1 (s, 1H); 8.2 (s, 1H); 8.5 (d, 1H).
Solvent: $CDCl_3$ 2.5 g of a TLC-pure product which is recrystallized from EtOH to give 2.3 g of 7-acetamido-4-benzyl-1-methyl-4H-[1,2,4]triazolo[4,3-a]quinazolin-5-one (example 4).
Yield: 33%
m.p (Tottoli): 316° C.
TLC: $R_f$=0.2 ($CH_2Cl_2$ 94/$CH_3OH$ 6)
$^1H$ NMR δ(ppm): 2.1 (s, 3H); 2.75 (s, 3H); 5.3 (s, 2H); 7.15–7.3 (m, 3H); 7.35 (d, 2H); 7.95–8.1 (m, 2H); 8.55 (s, 1H); 10.35 (s, 1H).
Solvent: DMSO Example 5

4-benzyl-1-cyclopentyl-7-(N-methylacetamido)-4H-[1,2,4]triazolo[4,3-a]quinazolin-5-one ($R^1$: 7-N-methylacetamido, $R^2$: cyclopentyl, $R^3$: benzyl)

0.27 g (0.67 mmol) of 7-acetamido-4-benzyl-1-cyclopentyl-4H-[1,2,4]triazolo[4,3-a]quinazolin-5-one (example 2) dissolved in 5 ml of dimethylformamide (DMF) is placed in a round-bottomed flask fitted with a stirrer, a dip thermometer, a nitrogen inlet and a condenser equipped with a moisture guard tube.

The solution is cooled to 0–5° C. under nitrogen stream and 0.016 g (0.67 mmol) of sodium hydride is added, with stirring. The solution is stirred for 30 min. Then, 0.42 ml (0.67 mmol) of methyl iodide is added in a single portion while keeping the temperature below 5° C. and stirring is continued for a further 1h30.

The solvent is evaporated off under vacuum and the residue is taken up in a mixture of water and ethyl acetate. The organic phase is separated out by settling, washed with saturated sodium chloride solution, dried over $Na_2SO_4$ and concentrated to dryness to give 0.2 g of crude product which is purified by chromatography on a column of silica, eluting with a 98.5 methylene chloride/1.5 methanol mixture. The pure fractions are combined and evaporated to give 0.07 g of pure product which is recrystallized from ethanol:
Yield: 25%
m.p (Tottoli): 194° C.
TLC: $R_f$=0.55 ($CH_2Cl_2$ 95/$CH_3OH$ 5)
$^1H$ NMR δ(ppm): 1.7–2.35 (m, 11 H); 3.2–3.4 (m, 3H); 3.6–3.7 (m, 1H); 5.5 (s, 2H); 7.2–7.35 (m, 3H); 7.55–7.8 (m, 3H); 7.95 (d, 1H); 8.3 (s, 1H).
Solvent: $CDCl_3$ Example 6

4-benzyl-1-cyclopentyl-7-(cyclopentyl-N-methylformamido)-4H-[1,2,4]triazolo[4,3-a]quinazolin-5-one ($R^1$: 7-cyclopentyl-N-methylformamido, $R^2$: cyclopentyl, $R^3$: benzyl)

1.25 g (0.274 mmol) of 4-benzyl-1-cyclopentyl-7-(cyclopentylformamido)-4H-[1,2,4]triazolo[4,3-a]quinazolin-5-one (example 1) dissolved in 12 ml of DMF is placed in a reactor fitted with a stirrer, a dip thermometer, a nitrogen inlet and a condenser equipped with a moisture guard tube.

0.066 g (0.274 mmol) of sodium hydride is added, under nitrogen stream, with stirring, at room temperature. The mixture is stirred for 45 min. Then, 0.17 ml (0.274 mmol) of methyl iodide is added in a single portion and the mixture is stirred for 2 h.

The solvent is evaporated off under vacuum and the residue is taken up in a mixture of water and ethyl acetate. The organic phase is separated out by settling, washed with a saturated sodium chloride solution, dried over $Na_2SO_4$ and concentrated to dryness to give 0.8 g of crude product (TLC-pure).
Yield: 62%
TLC: $R_f$=0.4 ($CH_2Cl_2$ 98/$CH_3OH$ 2)
$^1H$ NMR δ(ppm): 1.55–2.0 (m, 12H); 2.05–2.25 (m, 4H); 2.55–2.65 (m, 1H); 3.35 (s, 3H); 3.55–3.65 (m, 1H); 5.5 (s, 2H); 7.2–7.35 (m, 3H); 7.6–7.8 (m, 3H); 8.0 (d, 1H); 8.3 (s, 1H).
Solvent: $CDCl_3$ Example 7

4-benzyl-1-cyclopentyl-7-methylamino-4H-[1,2,4]triazolo[4,3-a]quinazolin-5-one ($R^1$: 7-N-methylamino, $R^2$: cyclopentyl, $R^3$: benzyl)

0.75 g (0.16 mmol) of 4-benzyl-1-cyclopentyl-7-(cyclopentyl-N-methylformamido)-4H-[1,2,4]triazolo[4,3-a]quinazolin-5-one (example 6) suspended in 15 ml of 6N hydrochloric acid solution is placed in a round-bottomed flask fitted with a stirrer and a condenser.

The suspension is heated to reflux for 45 min with stirring. After cooling, a saturated sodium bicarbonate solution is added to obtain an alkaline solution which is extracted 3 times with ethyl acetate. The combined organic phases are washed with a saturated sodium chloride solution and dried over $Na_2SO_4$. The solvent is evaporated off under vacuum to give 0.53 g of crude product which is purified by chromatography on a column of silica, eluting with a 98.5 methylene chloride/1.5 methanol mixture to provide 0.45 g of a TLC-pure product which is recrystallized from ethanol.

Yield: 75% m.p (Tottoli): 277° C.

TLC: $R_f$=0.4 ($CH_2Cl_2$ 97/$CH_3OH$ 3)

$^1$H NMR δ(ppm): 1.6–1.9 (m, 4H); 2–2.25 (m, 4H); 2.85 (s, 3H); 3.45–3.55 (m, 1H); 4.0–4.1 (m, 1H); 5.45 (s, 2H); 6.8 (d, 1H); 7.1–7.3 (m, 3H); 7.4 (s, 1H); 7.55–7.7 (m, 3H).

Solvent: $CDCl_3$

Example 8

4-(4-cyanobenzyl)-1-cyclopentyl-7-(N-methylacetamido)-4H-[1,2,4]triazolo[4,3-a] quinazolin-5-one ($R^1$: 7-N-methylacetamido, $R^2$: cyclopentyl, $R^3$: 4-cyanobenzyl)

a) synthesis of intermediate 1: 1-cyclopentyl-7-(N-methylacetamido)-4H-[1,2,4]triazolo[4,3-a]quinazolin-5-one 0.9 g (2.16 mmol) of 4-benzyl-1-cyclopentyl-7-(N-methylacetamido)-4H-[1,2,4]triazolo[4,3-a]quinazolin-5-one (example 5) dissolved in 90 ml of methanol is placed in a round-bottomed flask fitted with a stirrer and a condenser.

0.27 g of 10% palladium-on-charcoal is added and hydrogen is introduced for 24 h at a temperature of 60° C. The catalyst is removed by filtration and the solvent is evaporated off under vacuum to provide 0.7 g of product.

b) synthesis of example 8: 4-(4-cyanobenzyl)-1-cyclopentyl-7-(N-methylacetamido)-4H-[1,2,4]triazolo[4,3-a]quinazolin-5-one Intermediate 1 is dissolved in 20 ml of DMF. 0.7 g (2.16 mmol) de cesium carbonate is added, then, the mixture is stirred at room temperature for 30 min. Then, 0.43 g (2.16 mmol) of 4-cyanobenzyle bromide is added in a single portion and the mixture is heated at 100° C. for 4 hours with stirring. The solvent is evaporated off under vacuum and the residue is taken up in a mixture of water and ethyl acetate. The organic phase is separated out by settling, washed with a saturated sodium chloride solution, dried over $Na_2SO_4$ and concentrated to give 1.0 g of crude product (TLC-pure) which is then purified by chromatography on a column of silica, eluting with a 98.8 methylene chloride/1.2 methanol mixture to obtain 0.76 g of a TLC-pure product which is recrystallized from ethanol.

Yield: 80% m.p (Tottoli): 272–273° C.

TLC: $R_f$=0.45 ($CH_2Cl_2$ 97/$CH_3OH$ 3)

$^1$H NMR δ(ppm): 1.75–2.3 (m, 11H); 3.25–3.5 (m, 3H); 3.6–3.75 (m, 1H); 5.55 (s, 2H); 7.6 (d, 2H); 7.6–7.75 (m, 1H); 7.8 (d, 2H); 8.05 (d, 1H); 8.3 (s, 1H).

Solvent: $CDCl_3$

Example 9

4-(4-cyanobenzyl)-1-cyclopentyl-7-(N-methylamino)-4H-[1,2,4]triazolo[4,3-a]quinazolin-5-one ($R^1$: 7-N-methylamino, $R^2$: cyclopentyl, $R^3$: 4-cyanobenzyl)

0.37 g (0.84 mmol) of 4-(4-cyanobenzyl)-1-cyclopentyl-7-(N-methylacetamido)-4H-[1,2,4]triazolo[4,3-a] quinazolin-5-one (example 8) suspended in 7.5 ml of 6N hydrochloric acid solution is placed in a round-bottomed flask fitted with a stirrer and a condenser.

The mixture is stirred and heated to reflux for 45 min. After cooling, a saturated sodium bicarbonate solution is added to obtain an alkaline solution which is extracted 3 times with ethyl acetate. The combined organic phases are washed with a saturated sodium chloride solution and dried over $Na_2SO_4$. The solvent is evaporated off under vacuum to give 0.3 g of crude product which is purified by chromatography on a column of silica, eluting with a 99 methylene chloride/1 methanol mixture and then a methanol gradient to obtain 0.195 g of a TLC-pure product which is recrystallized from ethanol.

Yield: 58% m.p (Tottoli): 262° C.

TLC: $R_f$=0.6 ($CH_2Cl_2$ 97/$CH_3OH$ 3)

$^1$H NMR δ(ppm): 1.7–2.0 (m, 4H); 2.1–2.3 (m, 4H); 2.95 (s, 3H); 3.55–3.65 (m, 1H); 4.2 (s, 1H); 5.5 (s, 2H); 7.0 (d, 1H); 7.5–7.65 (m, 3H); 7.7–7.85 (m, 3H).

Solvent: $CDCl_3$

Example 10

4-benzyl-7-bromo-1-cyclopentyl-4H-[1,2,4]triazolo [4,3-a]quinazolin-5-one ($R^1$: 7-Br, $R^2$: cyclopentyl, $R^3$: benzyl)

a) synthesis of intermediate 2: 3-benzyl-6-bromo-2-(cyclopentylcarbonylhydrazino)-4H-quinazolin-4-one 0.8 g (2.3 mmol) of 3-benzyl-6-bromo-2-hydrazino-3,4-dihydro-quinazolin-4-one (synthesized according to a process described in patent application WO 00/66584) suspended in 10 ml of glacial acetic acid is placed in a round-bottomed flask equipped with a stirrer and a condenser. 0.34 g (2.54 mmol) of cyclopentylformyle chloride is added in a portionwise manner with stirring. The solution obtained is heated to reflux for 20 min. The solvent is evaporated off under vacuum and the residue is taken up in water.

The suspension is extracted 3 times with ethyl acetate, the combined organic phases are washed with a saturated aqueous solution of sodium chloride, dried over $Na_2SO_4$ and then concentrated under vacuum to give 1.0 g of crude product which is purified by chromatography on a column of silica, eluting with a 99.2 methylene chloride/0.8 methanol mixture. 0.6 g of TLC-pure product are obtained.

b) synthesis of example 10: 4-benzyl-7-bromo-1-cyclopentyl-4H-[1,2,4]triazolo[4,3-a]quinazolin-5-one 0.5 g (1.13 mmol) of 3-benzyl-6-bromo-2-(cyclopentylcarbonylhydrazino)-4H-quinazolin-4-one (intermediate 2) is placed in a round-bottomed flask which is heated until melting of the solid. The product is then heated for 4 min. After cooling, the crude product is dissolved in methylene chloride and directly purified by chromatography on a column of silica, eluting with a 99.6 methylene chloride/0.4 methanol mixture and then with a 99.2 methylene chloride/0.8 methanol mixture. The TLC-pure fractions are combined and concentrated off under vacuum to give 0.26 g of TLC-pure product:

Yield: 26%

TLC: $R_f$=0.4 ($CH_2Cl_2$ 98.5/$CH_3OH$ 1.5)

$^1$H NMR δ(ppm): 1.6–1.9(m, 4H); 1.95–2.25 (m, 4H); 3.45–3.6 (m, 1H); 5.45 (s, 2H); 7.1–7.3 (m, 3H); 7.55–7.85 (m, 4H); 8.55 (s, 1H).

Solvent: $CDCl_3$

Example 11

4-benzyl-7-bromo-1-methyl-4H-[1,2,4]triazolo[4,3-a]quinazolin-5-one ($R^1$: 7-Br, $R^2$: methyl, $R^3$: benzyl)

The compound of example 8 is prepared by the procedure described in example 7 using appropriate intermediates and reagents.

Yield: 52% m.p (Tottoli): 212° C.

TLC: $R_f$=0.25 ($CH_2Cl_2$ 98/$CH_3OH$ 2)

$^1$H NMR δ(ppm): 2.9(s, 3H); 5.5 (s, 2H); 7.2–7.3 (m, 3H); 7.7(d, 2H); 7.75 (d, 1H); 7,9 (d, 1H); 8.6 (s, 1H).

Solvent: $CDCl_3$

Evaluation of the In vitro Activity of the Compounds of the Invention

The capacity of the compounds of formula (I) of the invention to inhibit cyclic nucleotide phosphodiesterases is evaluated by measuring their $IC_{50}$ (concentration required to inhibit 50% of the enzymatic activity).

The type 4 phosphodiesterases are obtained from a cytosolic preparation extracted from a cell line U937 of human origin according to the method adapted from T. J. Torphy et al., J. Pharm. Exp. Ther. (1992), 263: 1195–1205.

The other types of phosphodiesterases are obtained from partial purification by FPLC on a Mono Q column (anion exchange column) according to a method adapted from Lavan B. E., Lakey T., Houslay M. D. Biochemical Pharmacology, (1989), 38(22), 4123–4136., and Silver P. J et al., Eur. J. Pharmacol. (1988) 150: 85–94, either from cell lines of human origin for PDE1 (TPH1 monocyte line) and PDE5 (MCF7 line obtained from an adenocarcinoma), or from dog aorta for PDE3, or, for human PDE3A, from cloning genes in SF21 insect cells into baculoviruses, according to the method adapted from Luckow, V. A. et al., in Recombinant DNA Technology&Applications., (1991) eds. Prokop, Bajpai, R. K.&Ho, C. S., pp 97–152.

The measurement of the enzymatic activity of the various types of PDE, and in particular the PDE4, is carried out according to a method adapted from W. J. Thompson et al., Advances in Cyclic Nucleotide Research, (1979) Vol. 10: 69–92, ed. G. Brooker et al. Raven Press, NY.

The substrate used is cGMP for PDE1 and PDE5 and cAMP for PDE 3 and PDE 4. The substrate concentration was 0.2 μM for PDE 1, PDE 3 and PDE 5, 0.25 μM for PDE 4.

The enzymatic reaction was stopped after 1 hour for PDE 1, PDE 3 and PDE 5 and 10 minutes for PDE 4.

In order to determine their $IC_{50}$, compounds of the invention were assayed at 8 to 11 concentrations ranging from 0.02 nM to 100 μM for PDE 4 and at 6 concentrations ranging from 0.1 μM to 30 μM for PDE 1, 3 and 5. The following table illustrates the inhibitory activity on PDE4 of some of the compounds of formula (I):

| Example | $IC_{50}$ (μM) |
|---------|----------------|
| 2 | 8.5 |
| 4 | 31 |
| 5 | 2.7 |
| 7 | 0.075 |
| 8 | 1.3 |
| 9 | 0.002 |
| 10 | 0.061 |
| 11 | 1 |

Examination of the results in the above table shows that the products of the invention tested in the assay inhibit the enzyme PDE4 in vitro effectively.

What is claimed is:

1. A compound of formula (I),

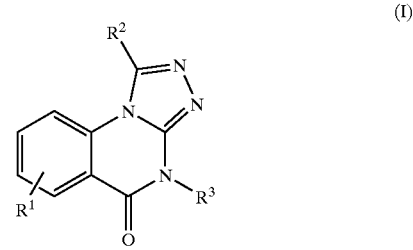

(I)

in which
  $R^1$ is:
    hydroxyl, halogen, nitro, mercapto, cyano or carboxyl, lower alkyl or lower alkoxy, these groups being optionally substituted with 1,2 or 3 halogen atoms, or
    —$NR^4R^5$ in which $R^4$ and $R^5$ are the same or different and are:
      H,
      lower alkyl, optionally substituted with 1,2 or 3 halogen, hydroxyl, cyano and lower alkoxy, or
      C(=O)$R^6$ in which $R^6$ is selected from:
        lower alkyl optionally substituted with $OR^7$, or $SR^7$ and
        —$X_1$-cycloalkyl optionally substituted with $OR^7$, $SR^7$, $NR^7R^8$ or with a linear or branched $C_1$–$C_4$ alkyl,
      in which $R^7$ and $R^8$ are the same or different and are hydrogen or lower alkyl and $X_1$ is a single bond or a linear or branched $C_1$–$C_4$ alkylene;
  $R^2$ is:
    lower alkyl optionally substituted with $OR^9$, $SR^9$, or
    —$X_2$-cycloalkyl optionally substituted with $OR^9$, $SR^9$, $NR^9R^{10}$ or with a linear or branched $C_1$–$C_4$ alkyl,
    in which $R^9$ and $R^{10}$ are the same or different and are hydrogen or lower alkyl and $X_2$ is a single bond or a linear or branched $C_{1-C4}$ alkylene; and
  $R^3$ is:

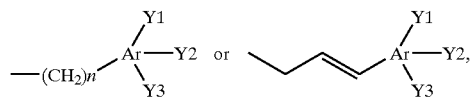

in which:
  n is an integer from 1 to 4,
  Ar is an aromatic ring comprising 5 or 6 atoms comprising zero to three O, S or N, and
  Y1, Y2 and Y3, which may be identical or different, are:
    hydrogen, hydroxyl, halogen, mercapto, nitro, C(=O)$R^{11}$, C(=O)O$R^{11}$, C(=O)$NR^{12}R^{13}$, $NR^{12}R^{13}$ or —$(CH_2)_s$CN in which s is an integer from 0 to 2;
    $R^{11}$, $R^{12}$ and $R^{13}$ are each independently hydrogen or lower alkyl, lower alkyl or lower alkoxy, each optionally substituted with 1, 2 or 3 halogen atoms, or —S(O)mR$^{14}$ in which m is 0 or 1 and R$^{14}$ is lower alkyl, an isomer thereof or a pharmaceutically acceptable salt thereof.

2. A compound of formula (I) according to claim 1, in which,

R$^1$ is:
  hydroxyl, halogen, nitro, mercapto, cyano or carboxyl, lower alkyl or lower alkoxy, these groups being optionally substituted with 1, 2 or 3 halogen atoms, or
  —NR$^4$R$^5$ in which R$^4$ and R$^5$ are the same or different and are:
    H,
    lower alkyl, optionally substituted with 1, 2 or 3 groups chosen from halogen, hydroxyl, cyano and lower alkoxy, or
    C(=O)R$^6$ in which R$^6$ is:
      lower alkyl optionally substituted with OR$^7$ or SR$^7$ or
      —X$_1$-cycloalkyl optionally substituted with OR$^7$, SR$^7$, NR$^7$R$^8$ or with a linear or branched C$_1$–C$_4$ alkyl,
in which R$^7$ and R$^8$ are the same or different and are hydrogen or lower alkyl and X$_1$ is a single bond or a linear or branched C$_1$–C$_4$ alkylene;

R$^2$ is:
  lower alkyl, or
  —X$_2$-cycloalkyl optionally substituted with a linear or branched C$_1$–C$_4$ alkyl, in which X$_2$ is a single bond or a linear or branched C$_1$–C$_4$ alkylene;

R$^3$ is:

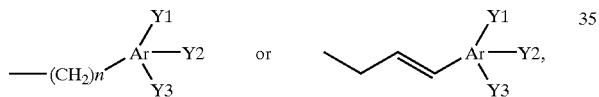

in which:
  n is 1,
  Ar is a phenyl or a pyridine, and
  Y1, Y2 and Y3, which may be identical or different, are:
    —hydrogen, methyl, methoxy, mercapto, nitro, C(=O)R$^{11}$, C(=O)OR$^{11}$, CONR$^{12}$R$^{13}$, NR$^{12}$R$^{13}$ or —(CH$_2$)$_s$CN in which s is an integer from 0 to 2 and R$^{11}$, R$^{12}$ and R$^{13}$ are hydrogen or lower alkyl.

3. A compound of formula (I) according to claim 2 in which

R$^1$ is:
  halogen and NH—R$^4$ in which R$^4$ is:
    C(=O)R$^6$ in which R$^6$ is hydrogen or lower alkyl, or lower alkyl;
  R$^2$ is lower alkyl or cycloalkyl;
  R$^3$ is a benzyl group optionally substituted with —(CH$_2$)$_s$CN in which s is an integer from 0 to 2.

4. A compound of formula (I) according to claim 3 in which

R$^1$ is:
  halogen or NH—R$^4$ in which R$^4$ is:
    C(=O)R$^6$ in which R$^6$ is hydrogen or methyl, or methyl;
  R$^2$ is methyl or cyclopentyl;
  R$^3$ a benzyl group optionally substituted with CN.

5. 4-Benzyl-1-cyclopentyl-7-(cyclopentylformamido)-4H [1,2,4]triazolo[4,3-a]quinazolin-5-one,
7-acetamido-4-benzyl-1-cyclopentyl-4H-[1,2,4] triazolo [4,3-a]quinazolin-5-one, 4-benzyl-7-(cyclopentylformamido)-1-methyl-4H-[1,2,4]triazolo[4,3-a]quinazolin-5-one, 7-acetamido4-benzyl-1-methyl-4H-[1,2,4]triazolol[4,3-a]quinazolin-5-one,
4-benzyl-1-cyclopentyl-7-(N-methylacetamido)-4H-[1,2,4]triazolo[4,3-a]quinazolin-5-one,
4-benzyl-1cyclopentyl-7-(cyclopentyl-N-methylformamido)-4H-[1,2,4]triazolo[4,3-a]quinazolin-5-one,
4-benzyl-1-cyclopentyl-7-methylamino-4H-[1, 2,4] triazolo[4,3-a]quinazolin-5-one, 4-(4-cyanobenzyl)-1cyclopentyl-7-(N-methylamino)-4H-[1,2,4]triazolo[4,3-a]quinazolin-5-one,
4-(4-cyanobenzyl)-1-cyclopentyl-7-(N-methylamino)-4H-[1,2,4]triazolo[4,3-a]quinazolin-5-one,
4-benzyl-7-bromo-1-cyclopentyl-4H-[1,2,4]triazolo[4,3-a]quinazolin-5-one, or 4-benzyl-7-bromo-1-methyl4H-[1,2,4]triazolo[4,3-a]quinazolin-5-one.

6. A process for preparing a compound according to claim 1 comprising (step 1) reacting a compound of the formula (1a)

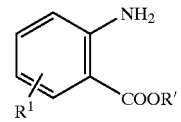

(1a)

in which is H or lower alkyl with a compound of the formula

R$^3$—N=C=S, to obtain a compound of the formula (1b)

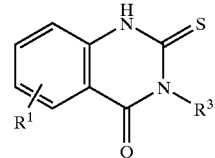

(1b)

(step 2) reacting a compound of the formula (1 b), with hydrazine hydrate, in an alcoholic solution, to obtain a compound of the formula (1c),

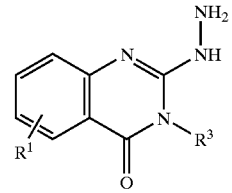

(1c)

and (step 3) cyclizing a compound of the formula (1c) by heating said compound of the formula (1c) in the presence of a compound of formula R$^2$—C(=O)Cl, to obtain a compound of formula (I)

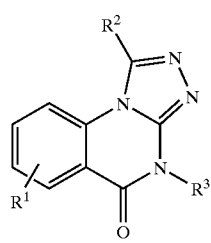

in which $R^1$ is:
hydroxyl, halogen, nitro, mercapto, cyano or carboxyl, lower alkyl or lower alkoxy, these groups being optionally substituted with 1,2 or 3 halogen atoms, or $NR^4R^5$ in which $R^4$ and $R^5$ are the same or different and are:
H,
lower alkyl, optionally substituted with 1,2 or 3 halogen, hydroxyl, cyano and lower alkoxy, or
$C(=O)R^6$ in which $R^6$ is:
lower alkyl optionally substituted with $OR^7$ or $SR^7$ or
$-X_1$-cycloalkyl optionally substituted with $OR^7$, $SR^7$, $NR^7R^8$ or with a linear or branched $C_1$–$C_4$ alkyl,
in which $R^7$ and $R^8$ are the same or different and are hydrogen or lower alkyl and $X_1$ is a single bond or a linear or branched $C_1$–$C_4$ alkylene;
$R^2$ is:
lower alkyl optionally substituted with $OR^9$, $SR^9$, or
$-X_2$-cycloalkyl optionally substituted with $OR^9$, $SR^9$, $NR^9R^{10}$ or with a linear or branched $C_1$–$C_4$ alkyl,
in which $R^9$ and $R^{10}$ are the same or different and are hydrogen or lower alkyl and $X_2$ is a single bond or a linear or branched $C_1$–$C_4$ alkylene; and $R^3$ is:

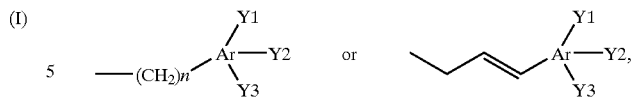

in which:
n is an integer from 1 to 4,
Ar is an aromatic ring comprising 5 or 6 atoms comprising zero to three O, S and N, and
Y1, Y2 and Y3, which may be identical or different, are:
hydrogen, hydroxyl, halogen, mercapto, nitro, $C(=O)R^{11}$, $C(=O)OR^{11}$, $C(=O)NR^{12}R^{13}$, $NR^{12}R^{13}$ or $-(CH_2)_sCN$ in which s is an integer from 0 to 2, $R^{11}$, $R^{12}$ and $R^{13}$ are hydrogen or lower alkyl,
lower alkyl or lower alkoxy, each optionally substituted with 1, 2 or 3 halogen atoms, or
$S(O)_mR^{14}$ in which m is 0 or 1 and $R^{14}$ is lower alkyl.

7. A pharmaceutical composition comprising a compound of formula (I) according to claim 1 in combination with a pharmaceutical acceptable excipient, diluent or carrier.

8. A method of treating asthma or chronic obstructive pulmonary disease in a mammal, which method comprises administering to said mammal an effective amount of a compound of claim 1 or a pharmaceutically acceptable salt thereof.

* * * * *